United States Patent [19]

Walker

[11] 4,172,141
[45] Oct. 23, 1979

[54] N-(NAPHTHYLETHYL)IMIDAZOLE DERIVATIVES

[75] Inventor: Keith A. M. Walker, Palo Alto, Calif.

[73] Assignee: Syntex (U.S.A.) Inc., Palo Alto, Calif.

[21] Appl. No.: 916,615

[22] Filed: Jun. 19, 1978

Related U.S. Application Data

[63] Continuation-in-part of Ser. No. 796,901, May 13, 1977, abandoned, which is a continuation of Ser. No. 666,388, Mar. 17, 1976, abandoned.

[51] Int. Cl.$^2$ ................ C07D 233/60; A61K 31/415
[52] U.S. Cl. .................................... 424/273 R; 548/341
[58] Field of Search ..................... 548/341; 424/273 R

[56] References Cited

U.S. PATENT DOCUMENTS

| | | | |
|---|---|---|---|
| 3,575,999 | 4/1971 | Godefroi et al. | 548/336 |
| 3,658,813 | 4/1972 | Godefroi et al. | 548/341 |
| 3,717,655 | 2/1973 | Godefroi et al. | 548/341 |
| 3,755,349 | 8/1973 | Timmler et al. | 548/341 |
| 3,764,690 | 10/1973 | Draber et al. | 548/341 |
| 3,796,704 | 3/1974 | Metzger et al. | 548/336 |
| 3,812,142 | 5/1974 | Meiser et al. | 548/341 |
| 3,839,574 | 10/1974 | Godefroi et al. | 548/336 |

FOREIGN PATENT DOCUMENTS 2504114 8/1975 Fed. Rep. of Germany ........... 548/341

OTHER PUBLICATIONS

Godefroi et al., J. Med. Chem. 1969, vol. 12, pp. 784–790.
Baggaley et al. J. Chem. Soc. (London) Perkin trans. 1 1975, pp. 1670–1671.

Primary Examiner—Natalie Trousof
Attorney, Agent, or Firm—Alan M. Krubiner

[57] ABSTRACT

Compounds of the formula

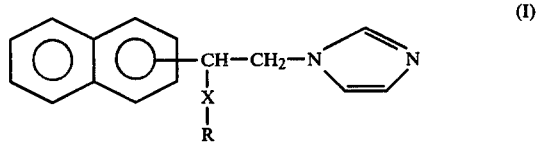

(I)

wherein R is alkyl, benzyl, substituted benzyl, phenyl or substituted phenyl, said substituted benzyl and substituted phenyl substituted on the phenyl ring with from one to three substituents independently selected from the group consisting of halo, lower alkyl and trifluoromethyl; X is oxygen or sulfur; and the pharmaceutically acceptable acid addition salts thereof are CNS-active agents, inhibitors of gastric secretion and antifungal, antibacterial and antiprotozoal agents.

28 Claims, No Drawings

N-(NAPHTHYLETHYL)IMIDAZOLE DERIVATIVES

RELATED APPLICATIONS

This is a continuation-in-part of co-pending application Ser. No. 796,901, now abandoned filed May 13, 1977, which in turn is a continuation of application Ser. No. 666,388, filed Mar. 17, 1976, now abandoned.

DESCRIPTION OF THE INVENTION

The present invention relates to certain substituted N-(naphthylethyl)imidazole derivatives. More particularly, the present invention relates to compounds of the formula

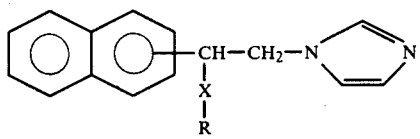

(I)

and the pharmaceutically acceptable acid addition salts thereof, wherein:

R is alkyl, benzyl, substituted benzyl, phenyl or substituted phenyl, said substituted benzyl and substituted phenyl substituted on the phenyl ring with from one to three substituents independently selected from the group consisting of halo, lower alkyl and trifluoromethyl; and X is oxygen or sulfur.

As used in the specification and appended claims, unless specified to the contrary, the following terms have the meaning indicated. The term "alkyl" refers to a straight or branched chain monovalent substituent consisting solely of carbon and hydrogen, containing no unsaturation and having from 1 to 12 carbon atoms. Examples of alkyl groups are methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl and the like. The term "lower alkyl" refers to the aforementioned groups having from 1 to 4 carbon atoms. The term "pharmaceutically acceptable acid addition salts" refers to salts of the subject compounds which possess the desired pharmacological or antimicrobial activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

All compounds of formula (I) possess at least one chiral center, i.e., the carbon atom to which are attached the naphthyl, X, CH₂ and H moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form but to encompass the individual optical isomers of the subject compounds.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of formula (I) or the alcohol precursors with an optically active acid, or by separation of the diastereomeric esters formed by reaction of the racemic alcohol precursors of compounds of formula (I) with an optically active acid or derivative thereof. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of formula (I) or the precursor alcohols.

Compounds of formula (I) exhibit a broad spectrum of CNS related activity such as anticonvulsant activity (as demonstrated by the maximal electroshock seizure test), anorexigenic, antidepressant and muscle relaxing activity; as well as activity of other types such as inhibition of gastric secretion and antihypertensive activities.

One aspect of the present invention relates to a method for treating and/or preventing convulsions in a mammalian subject comprising administering a therapeutically effective amount of a compound of formula (I), or a pharmaceutically acceptable acid addition salt thereof. Another aspect of the present invention relates to pharmaceutical compositions useful for the treatment and/or prevention of convulsions in a mammalian subject comprising a compound of formula (I), or a pharmaceutically acceptable acid addition salt thereof, in admixture with a pharmaceutically acceptable non-toxic carrier.

Yet another aspect of the present invention relates to a method for inhibiting gastric secretion in a mammalian subject comprising administering a therapeutically effective amount of a compound of formula (I), or a pharmaceutically acceptable acid addition salt thereof. Still another aspect of the present invention relates to pharmaceutical compositions useful for the inhibition of gastric secretion in a mammalian subject comprising a compound of formula (I), or a pharmaceutically acceptable acid addition salt thereof, in admixture with a pharmaceutically acceptable non-toxic carrier.

For the above described methods and compositions compounds of formula (I) wherein R is alkyl, preferably lower alkyl, are especially noteworthy.

In the practice of the above described methods of the present invention a therapeutically effective amount of the compound of formula (I) or a pharmaceutical composition containing same is administered via any of the usual and acceptable methods known in the art, either singly or in combination with another compound or compounds of the present invention or other pharmaceutical agents. These compounds or compositions can thus be administered orally or parenterally (i.e. intramuscularly, subcutaneously and intravenously), and can be administered either in the form of solid or liquid dosages including tablets, solutions, suspensions, and the like, as discussed in more detail hereinbelow. Oral administration is preferred.

The administration can be conducted in a single unit dosage form with continuous therapy or in single dosage therapy ad libitum. The method of the present invention may be practiced when relief of symptoms is specifically required, i.e. therapeutically, or as continuous or prophylactic treatment.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount for anticonvulsant use ranges from about 0.1 to about 300 mg./kg. body weight per day and preferably from about 1 to about 100 mg./kg. body weight per day. In alternative terms, for an average adult human subject, a therapeutically effective amount in accordance herewith would be, in preferred embodiments, from about 70 mg. to about 7 g. per day per subject. A therapeutically effective amount for inhibition of gastric secretion ranges from about 0.1 to about 300 mg./kg. body weight per day and preferably from about 0.25 to about 100 mg./kg. body weight per day. In alternative terms, for an average adult human subject, a therapeutically effective amount in accordance herewith would be, in preferred embodiments, from about 18 mg. to about 7 g per day per subject.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject.

Compounds of Formula I, particularly those wherein R is phenyl or benzyl, or phenyl or benzyl substituted with methyl, chloro or fluoro, are particularly useful as antifungal, antibacterial and antiprotozoal agents. The details of using such compounds and compositions containing same are substantially identical to those set forth for the compounds described in U.S. Pat. No. 4,078,071, column 2, line 38 to column 5, line 2 which is hereby incorporated by reference herein.

The compounds embraced by generic formula (I) can be represented subgenerically as:

wherein R is as defined above.

Preferred compounds of formula (I) are those wherein R is alkyl (preferably lower alkyl).

The present invention, in a still further aspect, is directed to methods for the preparation of the subject compounds of formula (I).

The following reaction sequence is directed to the preparation of certain compounds of formula (Ia).

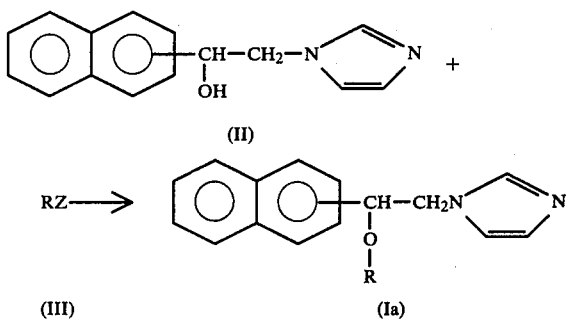

wherein R is as previously defined, excepting phenyl or substituted phenyl, and Z is a conventional leaving group such as a halide (e.g. chloride, bromide or iodide) or a sulfonate ester (e.g. methanesulfonate or p-toluenesulfonate).

In the above sequence, the hydroxy compounds of formula (II) are converted to the final products of formula (Ia) by O-alkylation with the appropriate RZ wherein Z is defined as above.

The alkylation is carried out by converting the hydroxy compound of formula (II) to a metal salt, preferably an alkali metal salt, by treatment with a strong base such as, for example, an (alkali) metal hydride such as sodium hydride or an (alkali) metal amide such as sodium amide or potassium amide and the like. This is preferably done in an inert organic solvent such as dimethylformamide, hexamethylphosphoramide, tetrahydrofuran and the like. The (alkali) metal salt is then contacted with RZ, preferably in the same solvent system, at a temperature between −20° and 100° C., most preferably between 0° and 60° C., for a period of 30 minutes to 18 hours.

Compounds of formula (Ia) wherein R is substituted or unsubstituted phenyl may be prepared from compounds of formula (II) by reaction with the corresponding phenol in the presence of a triarylphosphine (preferably triphenylphosphine) and a dialkyl azodicarboxylate (preferably dimethyl or diethyl azodicarboxylate). This reaction is preferably carried out in an inert solvent such as an ether (preferably tetrahydrofuran or diethyl ether), a hydrocarbon (preferably benzene or toluene) or dimethylformamide at a temperature between about 0° and 40° C.

Compounds of formula (Ia) may also be prepared by reaction of a compound of formula (IV) with imidazole as illustrated in the following reaction sequence:

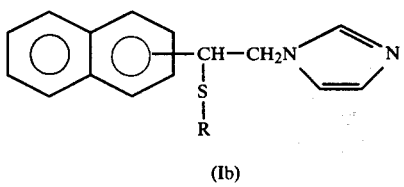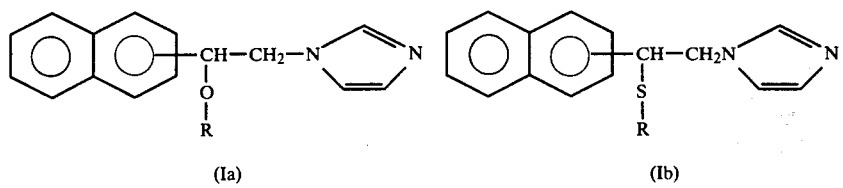

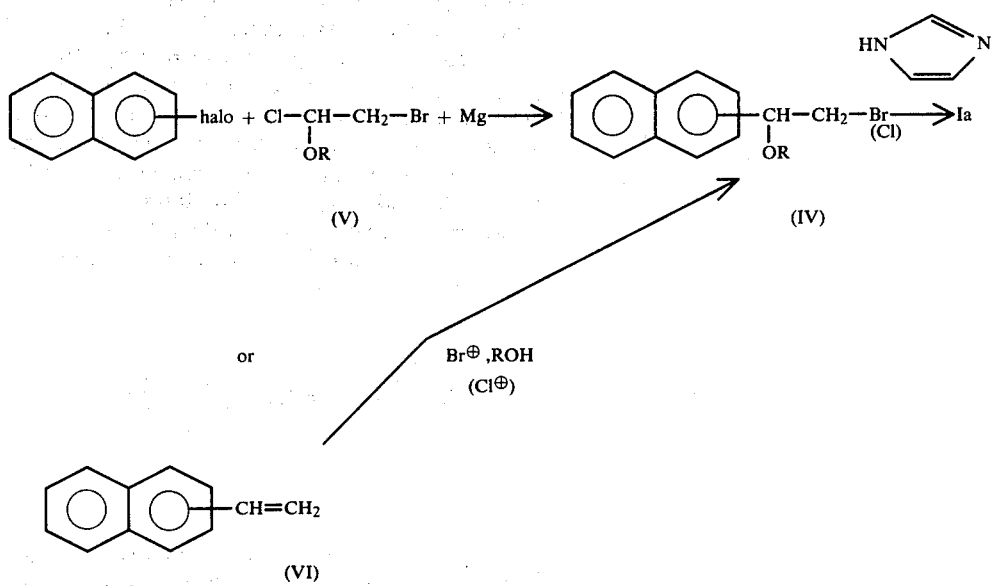

In this method the compound of formula (IV) is reacted with imidazole in a solvent such as acetonitrile, tetrahydrofuran or dimethylformamide, preferably acetonitrile or dimethylformamide, at a temperature between about 0° and 150° C., preferably between about 50° and 120° C., for a period of between about 1 and 72 hours.

The compound of formula (IV) may be prepared by reaction of a compound of formula (V) with a halonaphthalene in a Grignard type reaction or via the intermediacy of a magnesium derivative, or by reaction of a vinylnaphthalene (VI) with a source of Br⊕ or Cl⊕ and the alcohol ROH.

The following reaction sequence is directed to the preparation of compounds of formula (Ib):

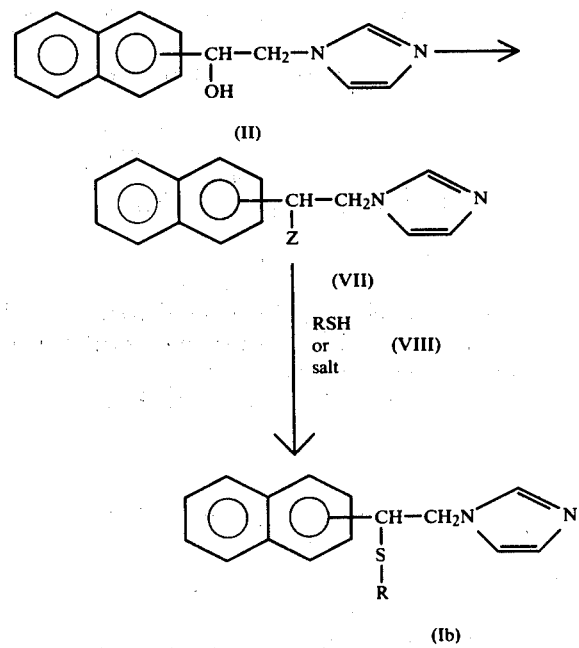

wherein R is as previously defined and Z is a conventional leaving group such as a halide (e.g., chloride or bromide) or a sulfonate ester (e.g., methanesulfonate or p-toluenesulfonate).

In the above sequence, compounds of formula (Ib) are prepared from the hydroxy compound of formula (II) by a two-step sequence involving conversion of the hydroxy group to a suitable leaving group such as a halide (e.g., a chloride or bromide) or a sulfonate ester (e.g., methanesulfonate or p-toluenesulfonate) which is then reacted with either a metal salt (preferably an alkali metal salt) of a thiol or thiophenol or with a thiol or thiophenol (preferably in the presence of base).

The conversion of the alcohol of formula (II) to the halide or sulfonate ester is carried out by means well known in the art. For example, the alcohol may be halogenated using a halogenating agent such as thionyl chloride or thionyl bromide, either neat, or in an inert organic solvent such as dichloromethane or chloroform, at a temperature between about −20° and 80° C., preferably between about 20° and 80° C. The halogenation reaction may be carried out in the presence of a molar equivalent of a base (e.g., pyridine) if desired. Alternative halogenation procedures include, for example, the use of triphenylphosphine with either carbon tetrachloride or carbon tetrabromide, or with N-chloro (or N-bromo)succinimide. When utilizing thionyl choride or thionyl bromide without the use of added base, the hydrochloride or hydrobromide salt of the corresponding halo compound is produced. This salt may be neutralized (e.g., with potassium carbonate) prior to its use in the thioalkylation step; however the salt may be used directly if excess thiol salt or thiophenol salt, or base is utilized.

Sulfonate esters may be prepared by the standard procedure of treating the alcohol with an excess of, for example, methanesulfonyl chloride or p-toluenesulfonyl chloride, in the presence of a base, for example pyridine or triethylamine. This reaction is carried out at a temperature from about −20° to 50° C., preferably between about 0° and 20° C.

The halide or sulfonate ester prepared as described above, is then reacted with either a metal salt (preferably an alkali metal salt such as a sodium or potassium salt) of a thiol or thiophenol or with a thiol or thiophenol (preferably in the presence of base). The reaction is carried out in the presence of an inert solvent at a temperature from about 0° to about 70° C.

The reaction of compounds of formula (VII) with compounds of formula (VIII) wherein R in formula (VIII) is alkyl, benzyl or substituted benzyl is carried out in an inert organic solvent such as, for example, tetrahydrofuran, diethyl ether, methanol and the like in the presence of a suitable base such as sodium hydride or sodium methoxide at a temperature of 0° to 70° C. for a period of 30 minutes to 18 hours.

The reaction of compounds of formula (VII) with compounds of formula (VIII) wherein R in formula (VIII) is phenyl or substituted phenyl is carried out in an inert organic solvent such as, for example, acetone, methanol and the like in the presence of a suitable base such as potassium carbonate, sodium hydroxide or sodium methoxide, preferably at ambient temperature to reflux for a period of 30 minutes to 18 hours.

Compounds of formula Ib may also be prepared from compounds of formula II by reaction with a tri(-loweralkyl)phosphine such as tri(n-butyl)phosphine and the corresponding sulfenimide as described in Tetrahedron Letters, No. 51, pp. 4475–4478 (1977).

The subject compounds of the instant invention can be isolated as free bases; however since many of the compounds in base form are oils or gums, it is often more convenient to isolate and further characterize the compounds as acid addition salts. These salts are prepared in the usual manner, i.e., by reaction of the base compound with a suitable inorganic or organic acid, described above. Salts formed with dibasic acids (e.g. oxalic acid) may generally contain one or two molecules of base per molecule of acid. All oxalates described herein contain one molecule of oxalic acid per molecule of imidazole base. If desired, the salts can be readily converted to the compounds in base form by treatment with a base, such as potassium or sodium carbonate or potassium or sodium hydroxide.

The alcohols required as starting materials for the preparation of the subject compounds of formula (I) may be prepared as follows:

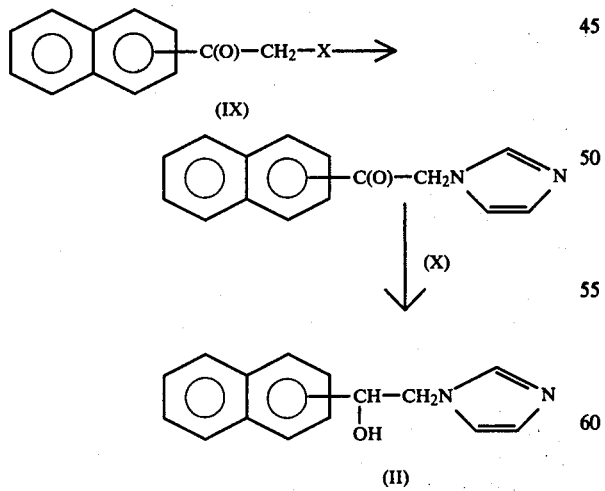

wherein X is bromo or chloro.

In the above reaction scheme the alcohols of formula (II) are prepared in a manner analogous to that described in U.S. Pat. No. 3,717,655 to Godefroi et al., e.g., by reaction of a halomethyl napthyl ketone (IX) with imidazole followed by reduction of the resultant 1-(naphthoylmethyl)imidazole (X) with a suitable reducing agent. The starting compounds of formula (IX) can be prepared according to conventional techniques, e.g., by halogenation of a methyl naphthyl ketone with bromine or chlorine in a suitable solvent such as carbon tetrachloride, or by halogenation of a methyl naphthyl ketone with cupric chloride or bromide in a suitable solvent such as ethyl acetate/chloroform.

In summary, another aspect of the present invention relates to a process for the preparation of a compound of the formula

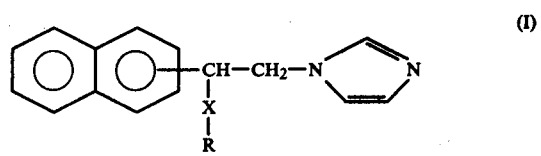

wherein:

R is alkyl, benzyl, substituted benzyl, phenyl or substituted phenyl, said substituted benzyl and substituted phenyl substituted on the phenyl ring with from one to three substituents selected from the group consisting of halo, lower alkyl and trifluoromethyl; and X is oxygen or sulfur; or a pharmaceutically acceptable acid addition salt thereof, which comprises:

(a) converting a compound of the formula

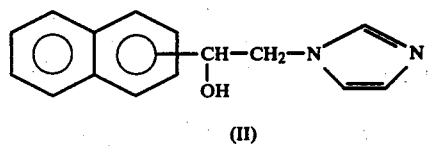

to an ether by reaction with base and RZ wherein R is as defined above, with the exclusion of phenyl and substituted phenyl, and Z is a conventional leaving group; or (b) converting a compound of the formula

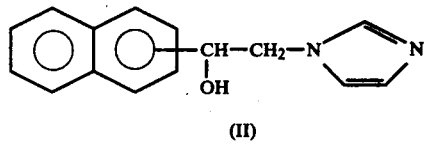

to an ether by reaction with a phenol ROH wherein R is phenyl or substituted phenyl, a triarylphosphine and a di(loweralkyl) azodicarboxylate; or (c) converting a compound of the formula

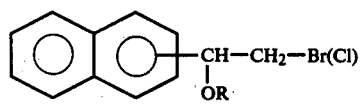

wherein R is as initially defined above, to an ether by reaction with imidazole; or (d) converting a compound of the formula

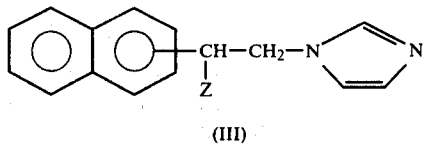

(III)

wherein Z is a conventional leaving group, or an acid addition salt thereof, to a thioether by reaction with RSH wherein R is as initially defined above; or (e) converting a compound of the formula

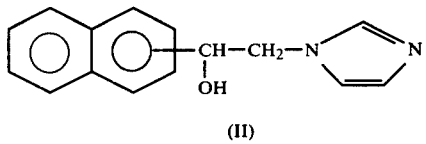

(II)

to a thioether by reaction with a tri(lower alkyl)phosphine and a sulfenimide; and (f) optionally converting a free base formed in any of steps (a) through (e) to an acid addition salt; or (g) optionally converting an acid addition salt formed in any of steps (a) through (f) to the corresponding free base.

The following specific description is given to enable those skilled in the art to more clearly understand and practice the invention. It should not be considered as a limitation upon the scope of the invention but merely as being illustrative and representative thereof.

PREPARATION A

To a stirred, ice-cooled slurry of 35 g. of imidazole in 25 ml. of dimethylformamide is added 24.9 g of bromomethyl 2-naphthyl ketone. The mixture is stirred for 2 hours at 0° C., and then allowed to come to room temperature and stirred overnight. The solution is poured into water and the resulting sticky solid filtered off, washed with water and dissolved in benzene. Thereafter the resultant benzene solution is dried (azeotroped) and the product precipitated by addition of ethereal hydrogen chloride. The salt is crystallized by the addition of ethyl acetate and the resulting solid recrystallized from methanol/acetone to yield colorless needles of 1-(2-naphthoylmethyl)imidazole hydrochloride, m.p. 226°–228.5° C. (decomp.).

To 9.4 g. of the above obtained 1-(2-naphthoylmethyl)imidazole hydrochloride in 200 ml. of methanol at 0°–5° C. is added, with stirring, excess sodium tetrahydroborate. After stirring for 30 minutes at 0° C., the reaction mixture is evaporated to dryness. The resultant residue is treated with 200 ml. of water and the product which crystallizes is filtered off, washed with water and recrystallized from ethyl acetate to yield 1-[2-(2-naphthyl)-2-hydroxyethyl]imidazole as off-white blades, m.p. 156°–160.5° C. (slight decomp.).

PREPARATION B

Methyl 1-naphthyl ketone (10.1 g.), in 50 ml. of a 1:1 mixture of chloroform and ethyl acetate is treated with 26.5 g. of copper (II) bromide. The resulting reaction mixture is heated under reflux with vigorous stirring until the evolution of hydrogen bromide ceases. When the reaction is complete the solvent is removed, ether is added and the copper (I) bromide is removed by filtration. Evaporation of the filtrate under reduced pressure yields crude bromomethyl 1-naphthyl ketone.

The above obtained bromomethyl 1-naphthyl ketone is then treated according to procedures previously recited in Preparation A to afford 1-[2-(1-naphthyl)-2-hydroxyethyl]imidazole, which, when recrystallized from ethyl acetate, yields snow white microcrystals, m.p. 112.5°–115° C. (slight decomp.).

EXAMPLE 1

To a solution of 2.38 g. of 1-[2-(2-naphthyl)-2-hydroxyethyl]imidazole in 40 ml. of hexamethylphosphoramide under nitrogen is added 480 mg. of a 56% dispersion of sodium hydride in mineral oil. After stirring for 1 hour at room temperature, the temperature is adjusted to 50° C. and stirring is continued for 1 to 2 hours. The reaction mixture is then cooled to about 5° C. and 0.74 ml. of iodomethane is added dropwise. Thereafter, the solution is stirred at 5° to 10° C. for 1 hour, then at room temperature for 4 hours and then heated at 50° C. for 2 hours. The reaction mixture is then poured into water and the resultant aqueous mixture extracted with ether and the ether extracts washed with water. The organic phase is dried over magnesium sulfate and evaporated. The resulting residue may be chromatographed on silica gel to effect purification of the free base. Elution of the gel with 5 to 10% methanol in dichloromethane yields 1-[2-(2-naphthyl)-2-(methoxy)ethyl]imidazole.

The hydrochloride salt of the free base is prepared by the dropwise addition of ethereal hydrogen chloride to the free base in ether. When precipitation is complete the salt is collected by filtration and recrystallized from ethyl acetate/methanol to yield 1-[2-(2-naphthyl)-2-(methoxy)ethyl]imidazole hydrochloride (1.32 g), m.p. 171.5°–172.5° C.

EXAMPLE 2

Thionyl chloride (5 ml.) and 2.0 g. of 1-[2-(2-naphthyl)-2-hydroxyethyl]imidazole are stirred at room temperature for about 20 minutes. Thereafter, the solution is evaporated to dryness and the residue is treated with ethyl acetate and filtered to yield 1-[2-(2-naphthyl)-2-chloroethyl]imidazole hydrochloride as a white solid.

The above obtained chloride, i.e., 1-[2-(2-naphthyl)-2-chloroethyl]imidazole hydrochloride (1.0 g.) is added to the salt prepared in situ from 1.60 g. of 4-chlorobenzyl mercaptan and 380 mg. of sodium hydride (56% dispersion in mineral oil) in 50 ml. of dry tetrahydrofuran. The mixture is stirred for 4 hours at 25° C. and then evaporated to dryness. The residue is extracted with ether and the ether extracts washed with water, dried over magnesium sulfate and evaporated. The resulting residue may be chromatographed on silica gel to effect purification of the free base. Elution of the gel with 5 to 10% acetone in dichloromethane yields 1-[2-(2-naphthyl)-2-(4-chlorobenzylthio)ethyl]imidazole.

The nitrate salt of the free base is prepared by the dropwise addition of concentrated nitric acid (d=1.42) to the free base in ether. When precipitation is complete the product is collected by filtration and recrystallized from ethyl acetate to yield 1-[2-(2-naphthyl)-2-(4-chlorobenzylthio)ethyl]imidazole nitrate, m.p. 126.5°–128.5° C. (decomp.).

EXAMPLE 3

1-[2-(1-naphthyl)-2-hydroxyethyl]imidazole (2.0 g.) and 5 ml. of thionyl chloride are stirred at room temperature for 30 minutes. Thereafter, the reaction mixture is evaporated to dryness and the residue treated with ethyl acetate and filtered to yield 1-[2-(1-naphthyl)-2-chloroethyl]imidazole hydrochloride as a white solid.

The above obtained chloro compound is then heated at reflux with vigorous stirring, with 1.1 g. of 3,4-dichlorothiophenol and 1.4 g. of anhydrous potassium carbonate in 50 ml. of acetone. After stirring for 2 hours the solvent is removed and water is added to the residue. The resultant aqueous mixture is then extracted with ether and the ether extracts washed with water, dried over magnesium sulfate and evaporated. The resulting residue is chromatographed on silica gel to effect purification of the free base. Elution with 5 to 10% acetone in dichloromethane yields 1-[2-(1-naphthyl)-2-(3,4-dichlorophenylthio)ethyl]imidazole.

The nitrate salt of the free base is prepared by the dropwise addition of concentrated nitric acid (d=1.42) to the free base in ether. When precipitation is complete the product is collected by filtration and recrystallized from acetone/ethyl acetate to yield 1-[2-(1-naphthyl)-2-(3,4-dichlorophenylthio)ethyl]imidazole nitrate, m.p. 151°–152° C. (decomp.).

EXAMPLE 4

To a mixture of 1.00 g of 1-[2-(2-naphthyl)-2-hydroxyethyl]imidazole, 0.81 g of p-chlorophenol and 0.92 g of diethyl azodicarboxylate in 20 ml. of dry tetrahydrofuran at room temperature was added 1.65 g of triphenylphosphine (with stirring). The resulting yellow solution was stirred overnight, the solvent evaporated and the residual oil dissolved in ether. The hydrochloride salt of the product was precipitated as a gum by dropwise addition of ethereal hydrogen chloride, and crystallized from ethyl acetate to give 1[2-(2-naphthyl)-2-(4-chlorophenoxy)ethyl]imidazole hydrochloride.

EXAMPLE 5

α-Bromomethyl-2-naphthylmethyl methyl ether is obtained by the method described in Bull. Soc. Chim., 25, 601–610 (1919) [Chem. Abs. 16, 1946 (1922)] or from 2-vinylnaphthalene by a procedure analogous to that described for styrene in, e.g., British Pat. No. 705,198 (1954) [Chem. Abs. 50, p 1911e (1956)].

A mixture of 60 -bromomethyl-2-naphthylmethyl methyl ether (2.40 g), imidazole (3.5 g) and a few ml. of acetonitrile are heated at 80° for 1 day and at 110° for 2 days. The mixture is then cooled, treated with water, extracted in ether the extracts washed, dried (MgSO4) and evaporated. The residue is chromatographed on silica gel eluting with 5–20% acetone in dichloromethane to give pure 1-[2-(2-naphthyl)-2-(methoxy)ethyl]imidazole, which was characterized as its hydrochloride salt as in Example 4.

EXAMPLE 6

N-(Phenylthio)phthalimide (1.92 g) is added to a mixture of 1.19 g. of 1-[2-(2-naphthyl)-2-hydroxyethyl]imidazole and 1.52 g of tri-n-butylphosphine in 30 ml. of dry tetrahydrofuran with stirring at room temperature. The solution is stirred overnight, the solvent removed and the residue dissolved in ether. The nitrate salt is precipitated by dropwise addition of concentrated nitric acid (d=1.42) until precipitation is complete, and the resulting 1-[2-(2-naphthyl)-2-(phenylthio)ethyl]imidazole nitrate filtered off and recrystallized from ethyl acetate.

EXAMPLE 7

Repeating the procedure in paragraph 1 of Example 1 using 1-[2-(1-naphthyl)-2-hydroxyethyl]imidazole or 1-[2-(2-naphthyl)-2-hydroxyethyl]imidazole as reactants of formula (II) and using appropriate halides as reactants of formula (III), or utilizng the procedure of Example 5 using the appropriate α-bromomethyl-1(or2-)naphthylmethyl R ether is productive of the following 1-[2-(naphthyl)-2-(R-oxy)ethyl]imidazoles which, where indicated, have been further characterized by conversion to the indicated acid addition salt:

1-[2-(1-naphthyl)-2-(methoxy)ethyl]imidazole,
1-[2-(1-naphthyl)-2-(ethoxy)ethyl]imidazole,
1-[2-(2-naphthyl)-2-(ethoxy)ethyl]imidazole-nitrate salt, m.p. 109°–110.5° C.,
1-[2-(1-naphthyl)-2-(n-propoxy)ethyl]imidazole,
1-[2-(2-naphthyl)-2-(n-propoxy)ethyl]imidazole,
1-[2-(1-naphthyl)-2-(isopropoxy)ethyl]imidazole,
1-[2-(2-naphthyl)-2-(isopropoxy)ethyl]imidazole,
1-[2-(1-naphthyl)-2-(n-butoxy)ethyl]imidazole,
1-[2-(2-naphthyl)-2-(n-butoxy)ethyl]imidazole,
1-[2-(1-naphthyl)-2-(isobutoxy)ethyl]imidazole,
1-[2-(2-naphthyl)-2-(isobutoxy)ethyl]imidazole,
1-[2-(1-naphthyl)-2-(sec-butoxy)ethyl]imidazole,
1-[2-(2-naphthyl)-2-(sec-butoxy)ethyl]imidazole,
1-[2-(1-naphthyl)-2-(tert-butoxy)ethyl]imidazole,
1-[2-(2-naphthyl)-2-(tert-butoxy)ethyl]imidazole,
1-[2-(1-naphthyl)-2-(n-pentoxy)ethyl]imidazole,
1-[2-(2-naphthyl)-2-(n-pentoxy)ethyl]imidazole,
1-[2-(1-naphthyl)-2-(n-hexyloxy)ethyl]imidazole,
1-[2-(2-naphthyl)-2-(n-hexyloxy)ethyl]imidazole,
1-[2-(1-naphthyl)-2-(n-heptyloxy)ethyl]imidazole,
1-[2-(2-naphthyl)-2-(n-heptyloxy)ethyl]imidazole,
1-[2-(1-naphthyl)-2-(n-octyloxy)ethyl]imidazole,
1-[2-(2-naphthyl)-2-(n-octyloxy)ethyl]imidazole,
1-[2-(1-naphthyl)-2-(n-nonyloxy)ethyl]imidazole,
1-[2-(2-naphthyl)-2-(n-nonyloxy)ethyl]imidazole,
1-[2-(1-naphthyl)-2-(n-decyloxy)ethyl]imidazole,
1-[2-(2-naphthyl)-2-(n-decyloxy)ethyl]imidazole,
1-[2-(1-naphthyl)-2-(n-undecyloxy)ethyl]imidazole,
1-[2-(2-naphthyl)-2-(n-undecyloxy)ethyl]imidazole,
1-[2-(1-naphthyl)-2-(n-dodecyloxy)ethyl]imidazole,
1-[2-(2-naphthyl)-2-(n-dodecyloxy)ethyl]imidazole,
1-[2-(1-naphthyl)-2-(benzyloxy)ethyl]imidazole,
1-[2-(2-naphthyl)-2-(benzyloxy)ethyl]imidazole,
1-[2-(1-naphthyl)-2-(4-methylbenzyloxy)ethyl]imidazole,
1-[2-(2-naphthyl)-2-(4-methylbenzyloxy)ethyl]imidazole,
1-[2-(1-naphthyl)-2-(4-tert-butylbenzyloxy)ethyl]imidazole,
1-[2-(2-naphthyl)-2-(4-tert-butylbenzyloxy)ethyl]imidazole,
1-[2-(1-naphthyl)-2-(2-bromobenzyloxy)ethyl]imidazole,
1-[2-(2-naphthyl)-2-(2-bromobenzyloxy)ethyl]imidazole,
1-[2-(1-naphthyl)-2-(3-bromobenzyloxy)ethyl]imidazole,
1-[2-(2-naphthyl)-2-(3-bromobenzyloxy)ethyl]imidazole,
1-[2-(1-naphthyl)-2-(4-bromobenzyloxy)ethyl]imidazole,
1-[2-(2-naphthyl)-2-(4-bromobenzyloxy)ethyl]imidazole, 1-[2-(1-naphthyl)-2-(2-chlorobenzyloxy)ethyl]imidazole,
1-[2-(2-naphthyl)-2-(2-chlorobenzyloxy)ethyl]imidazole,
1-[2-(1-naphthyl)-2-(4-chlorobenzyloxy)ethyl]imidazole,
1-[2-(2-naphthyl)-2-(4-chlorobenzyloxy)ethyl]imidazole,
1-[2-(1-naphthyl)-2-(2-fluorobenzyloxy)ethyl]imidazole,
1-[2-(2-naphthyl)-2-(2-fluorobenzyloxy)ethyl]imidazole,
1-[2-(1-naphthyl)-2-(4-fluorobenzyloxy)ethyl]imidazole,
1-[2-(2-naphthyl)-2-(4-fluorobenzyloxy)ethyl]imidazole,
1-[2-(1-naphthyl)-2-(2,4-dichlorobenzyloxy)ethyl]imidazole,
1-[2-(2-naphthyl)-2-(2,4-dichlorobenzyloxy)ethyl]imidazole,
1-[2-(1-naphthyl)-2-(3,4-dichlorobenzyloxy)ethyl]imidazole,
1-[2-(2-naphthyl)-2-(3,4-dichlorobenzyloxy)ethyl]imidazole,
1-[2-(1-naphthyl)-2-(3-trifluoromethylbenzyloxy)ethyl]imidazole,
1-[2-(2-naphthyl)-2-(3-trifluoromethylbenzyloxy)ethyl]imidazole,
1-[2-(1-naphthyl)-2-(4-trifluoromethylbenzyloxy)ethyl]imidazole, and
1-[2-(2-naphthyl)-2-(4-trifluoromethylbenzyloxy)ethyl]imidazole.

EXAMPLE 8

Repeating the procedure in paragraphs 1 and 2 of Example 2 using 1-[2-(1-naphthyl)-2-hydroxyethyl]imidazole or 1-[2-(2-napthyl)-2-hydroxyethyl]imidazole as reactant of formula (II) and using appropriate thiols as reactants of formula (VIII) is productive of the following 1-[2-(naphthyl)-2-(R-thio)ethyl]imidazoles, which, where indicated, have been further characterized by conversion to the indicated acid addition salt:

1-[2-(1-naphthyl)-2-(methylthio)ethyl]imidazole,
1-[2-(2-naphthyl)-2-(methylthio)ethyl]imidazole,
1-[2-(1-naphthyl)-2-(ethylthio)ethyl]imidazole,
1-[2-(2-naphthyl)-2-(ethylthio)ethyl]imidazole,
1-[2-(1-naphthyl)-2-(n-propylthio)ethyl]imidazole,
1-[2-(2-naphthyl)-2-(n-propylthio)ethyl]imidazole,
1-[2-(1-naphthyl)-2-(isopropylthio)ethyl]imidazole,
1-[2-(2-napthyl)-2-(isopropylthio)ethyl]imidazole,
1-[2-(1-naphthyl)-2-(n-butylthio)ethyl]imidazole,
1-[2-(2-naphthyl)-2-(n-butylthio)ethyl]imidazole,
1-[2-(1-naphthyl)-2-(isobutylthio)ethyl]imidazole,
1-[2-(2-naphthyl)-2-(isobutylthio)ethyl]imidazole,
1-[2-(1-naphthyl)-2-(sec-butylthio)ethyl]imidazole,
1-[2-(2-naphthyl)-2-(sec-butylthio)ethyl]imidazole,
1-[2-(1-naphthyl)-2-(tert-butylthio)ethyl]imidazole,
1-[2-(2-naphthyl)-2-(tert-butylthio)ethyl]imidazole,
1-[2-(1-naphthyl)-2-(n-pentylthio)ethyl]imidazole,
1-[2-(2-naphthyl)-2-(n-pentylthio)ethyl]imidazole,
1-[2-(1-napthyl)-2-(n-hexylthio)ethyl]imidazole,
1-[2-(2-naphthyl)-2-(n-hexylthio)ethyl]imidazole,
1-[2-(1-naphthyl)-2-(n-heptylthio)ethyl]imidazole,
1-[2-(2-naphthyl)-2-(n-heptylthio)ethyl]imidazole,
1-[2-(1-naphthyl)-2-(n-octylthio)ethyl]imidazole,
1-[2-(2-naphthyl)-2-(n-octylthio)ethyl]imidazole,
1-[2-(1-naphthyl)-2-(n-nonylthio)ethyl]imidazole,
1-[2-(2-naphthyl)-2-(n-nonylthio)ethyl]imidazole,
1-[2-(1-naphthyl)-2-(n-decylthio)ethyl]imidazole,
1-[2-(2-naphthyl)-2-(n-decylthio)ethyl]imidazole,
1-[2-(1-naphthyl)-2-(benzylthio)ethyl]imidazole,
1-[2-(2-naphthyl)-2-(benzylthio)ethyl]imidazole,
1-[2-(1-naphthyl)-2-(2-chlorobenzylthio)ethyl]imidazole,
1-[2-(2-naphthyl)-2-(2-chlorobenzylthio)ethyl]imidazole,
1-[2-(1-naphthyl)-2-(4-chlorobenzylthio)ethyl]imidazole, nitrate salt m.p. 133.5°–135° C. (decomp.)
1-[2-(1-naphthyl)-2-(2,4-dichlorobenzylthio)ethyl]imidazole,
1-[2-(2-naphthyl)-2-(2,4-dichlorobenzylthio)ethyl]imidazole,
1-[2-(1-naphthyl)-2-(3,4-dichlorobenzylthio)ethyl]imidazole,
1-[2-(2-naphthyl)-2-(3,4-dichlorobenzylthio)ethyl]imidazole,
1-[2-(1-naphthyl)-2-(2-fluorobenzylthio)ethyl]imidazole,
1-[2-(2-naphthyl)-2-(2-fluorobenzylthio)ethyl]imidazole,
1-[2-(1-naphthyl)-2-(4-fluorobenzylthio)ethyl]imidazole,
1-[2-(2-naphthyl)-2-(4-fluorobenzylthio)ethyl]imidazole,
1-[2-(1-naphthyl)-2-(2-bromobenzylthio)ethyl]imidazole,
1-[2-(2-naphthyl)-2-(2-bromobenzylthio)ethyl]imidazole,
1-[2-(1-naphthyl)-2-(3-bromobenzylthio)ethyl]imidazole,
1-[2-(2-naphthyl)-2-(3-bromobenzylthio)ethyl]imidazole,
1-[2-(1-naphthyl)-2-(4-bromobenzylthio)ethyl]imidazole,
1-[2-(2-naphthyl)-2-(4-bromobenzylthio)ethyl]imidazole,
1-[2-(1-naphthyl)-2-(3-trifluoromethylbenzylthio)ethyl]imidazole,
1-[2-(2-naphthyl)-2-(3-trifluoromethylbenzylthio)ethyl]imidazole,
1-[2-(1-naphthyl)-2-(4-trifluoromethylbenzylthio)ethyl]imidazole,
1-[2-(2-naphthyl)-2-(4-trifluoromethylbenzylthio)ethyl]imidazole,
1-[2-(1-naphthyl)-2-(4-methylbenzylthio)ethyl]imidazole,
1-[2-(2-naphthyl)-2-(4-methylbenzylthio)ethyl]imidazole,
1-[2-(1-naphthyl)-2-(4-tert-butylbenzylthio)ethyl]imidazole,
1-[2-(2-naphthyl)-2-(4-tert-butylbenzylthio)ethyl]imidazole,
1-[2-(1-naphthyl)-2-(n-undecylthio)ethyl]imidazole,
1-[2-(2-naphthyl)-2-(n-undecylthio)ethyl]imidazole,
1-[2-(1-naphthyl)-2-(n-dodecylthio)ethyl]imidazole, and
1-[2-(2-naphthyl)-2-(n-dodecylthio)ethyl]imidazole.

EXAMPLE 9

Repeating the procedure in paragraphs 1 and 2 of Example 3, or the procedure in Example 6, using 1-[2-(1-naphthyl)-2-hydroxyethyl]imidazole or 1-[2-(2-naphthyl)-2-hydroxyethyl]imidazole as reactants of formula (II) and using appropriate thiophenols as reactants of formula (VIII) or the appropriate sulfenimide is productive of the following compounds which, where indicated, have been further characterized by conversion to the indicated acid addition salts:

1-[2-(1-naphthyl)-2-(phenylthio)ethyl]imidazole,
1-[2-(1-naphthyl)-2-(4-chlorophenylthio)ethyl-]imidazole,
1-[2-(2-naphthyl)-2-(4-chlorophenylthio)ethyl-]imidazole,
1-[2-(1-naphthyl)-2-(2,4-dichlorophenylthio)ethyl-]imidazole,
1-[2-(2-naphthyl)-2-(2,4-dichlorophenylthio)ethyl-]imidazole,
1-[2-(1-naphthyl)-2-(2,6-dichlorophenylthio)ethyl-]imidazole,
1-[2-(2-naphthyl)-2-(2,6-dichlorophenylthio)ethyl-]imidazole,
1-[2-(2-naphthyl)-2-(3,4-dichlorophenylthio)ethyl-]imidazole, nitrate salt m.p. 158°–161.5° C. (decomp.),
1-[2-(1-naphthyl)-2-(2,4,5-trichlorophenylthio)ethyl-]imidazole,
1-[2-(2-naphthyl)-2-(2,4,5-trichlorophenylthio)ethyl-]imidazole - nitrate salt, m.p. 205°–106° C. (foams),
1-[2-(1-naphthyl)-2-(3,4,5-trichlorophenylthio)ethyl-]imidazole,
1-[2-(2-naphthyl)-2-(3,4,5-trichlorophenylthio)ethyl-]imidazole,
1-[2-(1-naphthyl)-2-(2,4,6-trichlorophenylthio)ethyl-]imidazole - nitrate salt, m.p. 192.5°–195° C.,
1-[2-(2-naphthyl)-2-(2,4,6-trichlorophenylthio)ethyl-]imidazole - nitrate salt, m.p. 202°–205.5° C.,
1-[2-(1-naphthyl)-2-(2-fluorophenylthio)ethyl-]imidazole,
1-[2-(2-naphthyl)-2-(2-fluorophenylthio)ethyl-]imidazole,
1-[2-(1-naphthyl)-2-(4-fluorophenylthio)ethyl-]imidazole,
1-[2-(2-naphthyl)-2-(4-fluorophenylthio)ethyl-]imidazole,
1-[2-(1-naphthyl)-2-(4-bromophenylthio)ethyl-]imidazole,
1-[2-(2-naphthyl)-2-(4-bromophenylthio)ethyl-]imidazole,
1-[2-(1-naphthyl)-2-(4-bromo-3-methylphenylthio)ethyl]imidazole,
1-[2-(2-naphthyl)-2-(4-bromo-3-methylphenylthio)ethyl]imidazole,
1-[2-(1-naphthyl)-2-(4-trifluoromethylphenylthio)ethyl-]imidazole,
1-[2-(2-naphthyl)-2-(4-trifluoromethylphenylthio)ethyl-]imidazole,
1-2-(1-naphthyl)-2-(2-methylphenylthio)ethyl-]imidazole,
1-[2-(2-naphthyl)-2-(2-methylphenylthio)ethyl-]imidazole,
1-[2-(1-naphthyl)-2-(3-methylphenylthio)ethyl-]imidazole,
1-[2-(2-naphthyl)-2-(3-methylphenylthio)ethyl-]imidazole,
1-[2-(1-naphthyl)-2-(4-methylphenylthio)ethyl-]imidazole,
1-[2-(2-naphthyl)-2-(4-methylphenylthio)ethyl-]imidazole,
1-[2-(1-naphthyl)-2-(3-ethylphenylthio)ethyl]imidazole,
1-[2-(2-naphthyl)-2-(3-ethylphenylthio)ethyl]imidazole,
1-[2-(1-naphthyl)-2-(2-isopropylphenylthio)ethyl-]imidazole,
1-[2-(2-naphthyl)-2-(2-isopropylphenylthio)ethyl-]imidazole,
1-[2-(1-naphthyl)-2-(4-tert-butylphenylthio)ethyl-]imidazole,
1-[2-(2-naphthyl)-2-(4-tert-butylphenylthio)ethyl-]imidazole,
1-[2-(1-naphthyl)-2-(4-tert-butyl-2-methylphenylthio)ethyl]imidazole,
1-[2-(2-naphthyl)-2-(4-tert-butyl-2-methylphenylthio)ethyl]imidazole,
1-[2-(1-naphthyl)-2-(2,6-dimethylphenylthio)ethyl-]imidazole,
1-[2-(2-naphthyl)-2-(2,6-dimethylphenylthio)ethyl-]imidazole,
1-[2-(1-naphthyl)-2-(2-chlorophenylthio)ethyl-]imidazole;
1-[2-(2-naphthyl)-2-(2-chlorophenylthio)ethyl-]imidazole;
1-[2-(1-naphthyl)-2-(2,5-dichlorophenylthio)ethyl-]imidazole;
1-[2-(2-naphthyl)-2-(2,5-dichlorophenylthio)ethyl-]imidazole;
1-[2-(1-naphthyl)-2-(2,5-dimethylphenylthio)ethyl-]imidazole, and
1-[2-(2-naphthyl)-2-(2,5-dimethylphenylthio)ethyl-]imidzole.

EXAMPLE 10

Repeating the procedure in Example 4 using 1-[2-(1-naphthyl)-2-hydroxyethyl]imidazole or 1-[2-(2-naphthyl)-2-hydroxyethyl]imidazole as reactants of formula (II) and the appropriate phenol, is productive of the following 1-[2-(naphthyl)-2-(R-oxy)ethyl]imidazoles which, where indicated, have been further characterized by conversion to the indicated acid addition salt:

1-[2-(1-naphthyl)-2-(phenoxy)ethyl]imidazole;
1-[2-(2-naphthyl)-2-(phenoxy)ethyl]imidazole,
1-[2-(1-naphthyl)-2-(2-methylphenoxy)ethyl]imidazole,
1-[2-(2-naphthyl)-2-(2-methylphenoxy)ethyl]imidazole,
1-[2-(1-naphthyl)-2-(3-methylphenoxy)ethyl]imidazole,
1-[2-(2-naphthyl)-2-(3-methylphenoxy)ethyl]imidazole,
1-[2-(1-naphthyl)-2-(4-methylphenoxy)ethyl]imidazole,
1-[2-(2-naphthyl)-2-(4-methylphenoxy)ethyl]imidazole,
1-[2-(1-naphthyl)-2-(2,6-dimethylphenoxy)ethyl-]imidazole,
1-[2-(2-naphthyl)-2-(2,6-dimethylphenoxy)ethyl-]imidazole,
1-[2-(1-naphthyl)-2-(2-fluorophenoxy)ethyl]imidazole,
1-[2-(2-naphthyl)-2-(2-fluorophenoxy)ethyl]imidazole,
1-[2-(1-naphthyl)-2-(2-chlorophenoxy)ethyl]imidazole,
1-[2-(2-naphthyl)-2-(2-chlorophenoxy)ethyl]imidazole,
1-[2-(1-naphthyl)-2-(2-bromophenoxy)ethyl]imidazole,
1-[2-(2-naphthyl)-2-(2-bromophenoxy)ethyl]imidazole,
1-[2-(1-naphthyl)-2-(4-fluorophenoxy)ethyl]imidazole,
1-[2-(2-naphthyl)-2-(4-fluorophenoxy)ethyl]imidazole,
1-[2-(1-naphthyl)-2-(4-chlorophenoxy)ethyl]imidazole,
1-[2-(1-naphthyl)-2-(3-fluorophenoxy)ethyl]imidazole,
1-[2-(2-naphthyl)-2-(3-fluorophenoxy)ethyl]imidazole,
1-[2-(1-naphthyl)-2-(2,4-dichlorophenoxy)ethyl-]imidazole,
1-[2-(2-naphthyl)-2-(2,4-dichlorophenoxy)ethyl-]imidazole,
1-[2-(1-naphthyl)-2-(3,4-dichlorophenoxy)ethyl-]imidazole,
1-[2-(2-naphthyl)-2-(3,4-dichlorophenoxy)ethyl-]imidazole, 1-[2-(1-naphthyl)-2-(2,4,5-trichlorophenoxy)ethyl]imidazole,
1-[2-(2-naphthyl)-2-(2,4,5-trichlorophenoxy)ethyl]imidazole,
1-[2-(1-naphthyl)-2-(2,4,6-trichlorophenoxy)ethyl]imidazole,
1-[2-(2-naphthyl)-2-(2,4,6-trichlorophenoxy)ethyl]imidazole,
1-[2-(1-naphthyl)-2-(3,4,5-trichlorophenoxy)ethyl]imidazole,
1-[2-(2-naphthyl)-2-(3,4,5-trichlorophenoxy)ethyl]imidazole,
1-[2-(1-naphthyl)-2-(3-ethylphenoxy)ethyl]imidazole,
1-[2-(2-naphthyl)-2-(3-ethylphenoxy)ethyl]imidazole,
1-[2-(1-naphthyl)-2-(2-isopropylphenoxy)ethyl]imidazole,
1-[2-(2-naphthyl)-2-(2-isopropylphenoxy)ethyl]imidazole,
1-[2-(1-naphthyl)-2-(4-tert-butylphenoxy)ethyl]imidazole,
1-[2-(2-naphthyl)-2-(4-tert-butylphenoxy)ethyl]imidazole,
1-[2-(1-naphthyl)-2-(4-tert-butyl-2-methylphenoxy)ethyl]imidazole,
1-[2-(2-naphthyl)-2-(4-tert-butyl-2-methylphenoxy)ethyl]imidzole,
1-[2-(1-naphthyl)-2-(4-trifluoromethylphenoxy)ethyl]imidazole,
1-[2-(2-naphthyl)-2-(4-trifluoromethylphenoxy)ethyl]imidazole,
1-[2-(1-naphthyl)-2-(4-bromo-3-methylphenoxy)ethyl]imidazole, and
1-[2-(2-naphthyl)-2-(4-bromo-3-methylphenoxy)ethyl]imidazole.

EXAMPLE 11

Ethereal hydrogen chloride is added dropwise to a stirred solution of 1.0 g. of 1-[2-(2-naphthyl)-2-(methoxy)ethyl]imidazole in 100 ml. of anhydrous ether until precipitation is complete. The product is filtered off, washed with ether, air dried and recrystallized from ethyl acetate/methanol to yield 1-[2-(2-naphthyl)-2-(methoxy)ethyl]imidazole hydrochloride, m.p. 171.5°-172.5° C.

In similar manner, all compounds of formula (I) in base form can be converted to the acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid or p-toluenesulfonic acid.

EXAMPLE 12

1-[2-(2-naphthyl)-2-(methoxy)ethyl]imidazole hydrochloride (800 mg.) in 50 ml. of dichloromethane is shaken with excess dilute potassium carbonate solution until the salt is completely neutralized. The organic layer is then separated, washed twice with water, dried over magnesium sulfate and evaporated to yield 1-[2-(2-naphthyl)-2-(methoxy)ethyl]-imidazole.

In similar manner, the acid addition salts of all compounds of formula (I) can be converted to the corresponding compounds in base form.

EXAMPLE 13

The following example illustrates the preparation of representative pharmaceutical formulations containing an active compound of Formula (I).

| A. Topical Formulation (e.g. for antimicrobial use) | |
|---|---|
| | grams |
| Active compound (e.g., 1-[2-(2-naphthyl)-2-(2,4-dichlorobenzylthio)ethyl]imidazole nitrate | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water    qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

| B. I.V. Formulation (e.g., for anticonvulsant use) | |
|---|---|
| Active compound, e.g. 1-[2-(2-naphthyl)-2-(methoxy)ethyl]-imidazole hydrochloride | 0.5 g. |
| Propylene glycol | 20 g. |
| Polyethylene glycol 400 | 20 g. |
| Tween 80 | 1 g. |
| 0.9% Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

| | parts by weight |
|---|---|
| Active compound, e.g. 1-[2-(2-naphthyl)-2-(methoxy)ethyl]-imidazole hydrochloride | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

What is claimed is:
1. A compound of the formula

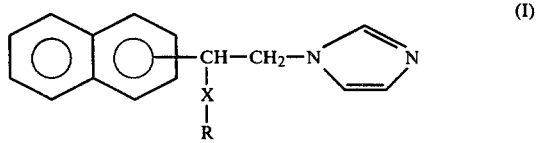

and the pharmaceutically acceptable, acid addition salts thereof, wherein:

R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl; and X is oxygen or sulfur.

2. A compound of claim 1 wherein X is oxygen.

3. A compound of claim 1 wherein X is sulfur.

4. A compound of claim 1 wherein R is alkyl having from 1 to 12 carbon atoms, benzyl, phenyl, or benzyl or phenyl substituted with methyl, chloro or fluoro.

5. A compound of claim 4 wherein R is lower alkyl having from 1 to 4 carbon atoms.

6. The compound of claim 4 which is 1-[2-(1-naphthyl)-2-(methoxy)ethyl]imidazole.

7. The compound of claim 4 which is 1-[2-(2-naphthyl)-2-(methoxy)ethyl]imidazole.

8. The compound of claim 4 which is 1-[2-(1-naphthyl)-2-(ethoxy)ethyl]imidazole.

9. The compound of claim 4 which is 1-[2-(2-naphthyl)-2-(ethoxy)ethyl]imidazole.

10. The compound of claim 4 which is 1-[2-(1-naphthyl)-2-(phenoxy)ethyl]imidazole.

11. The compound of claim 4 which is 1-[2-(2-naphthyl)-2-(phenoxy)ethyl]imidazole.

12. The compound of claim 4 which is 1-[2-(1-naphthyl)-2-(2,4-dichlorobenzyloxy)ethyl]imidazole.

13. The compound of claim 4 which is 1-[2-(2-naphthyl)-2-(2,4-dichlorobenzyloxy)ethyl]imidazole.

14. The compound of claim 4 which is 1-[2-(1-naphthyl)-2-(4-chlorobenzyloxy)ethyl]imidazole.

15. The compound of claim 4 which is 1-[2-(2-naphthyl)-2-(4-chlorobenzyloxy)ethyl]imidazole.

16. The compound of claim 4 which is 1-[2-(2-naphthyl)-2-(2,4-dichlorobenzylthio)ethyl]imidazole.

17. The compound of claim 4 which is 1-[2-(2-naphthyl)-2-(4-chlorobenzylthio)ethyl]imidazole.

18. The compound of claim 4 which is 1-[2-(2-naphthyl)-2-(2,4,6-trichlorophenylthio)ethyl]imidazole.

19. The compound of claim 4 which is 1-[2-(2-naphthyl)-2-(2,5-dichlorophenylthio)ethyl]imidazole.

20. The compound of claim 4 which is 1-[2-(2-naphthyl)-2-(2,6-dichlorophenylthio)ethyl]imidazole.

21. A method for treating and preventing convulsions in a mammalian subject comprising administering to said subject a therapeutically effective amount of a compound of the formula

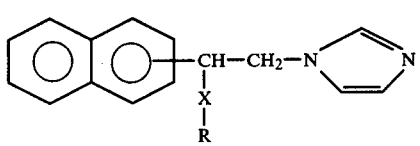

(I)

and the pharmaceutically acceptable, acid addition salts thereof, wherein:

R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl; and X is oxygen or sulfur; or a pharmaceutical composition containing such compound as an active ingredient.

22. A pharmaceutical composition for the prevention and treatment of convulsions in mammals comprising a therapeutically effective amount of a compound of the formula

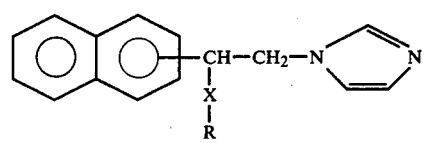

(I)

and the pharmaceutically acceptable, acid addition salts thereof, wherein:

R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl; and X is oxygen or sulfur; in admixture with a pharmaceutically acceptable, non-toxic carrier.

23. The composition of claim 22 wherein R is lower alkyl.

24. A method for inhibiting gastric secretion in a mammalian subject comprising administering to said subject a therapeutically effective amount of a compound of the formula

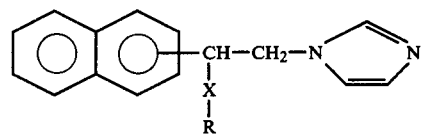

(I)

and the pharmaceutically acceptable, acid addition salts thereof, wherein:

R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl; and X is oxygen or sulfur or a pharmaceutical composition containing such compound as an active ingredient.

25. A pharmaceutical composition for inhibiting gastric secretion in mammals comprising a therapeutically effective amount of a compound of the formula

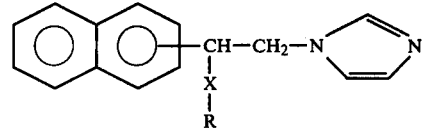

(I)

and the pharmaceutically acceptable, acid addition salts thereof, wherein:

R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl; and X is oxygen or sulfur; in admixture with a pharmaceutically acceptable, non-toxic carrier.

26. A method of inhibiting the growth of fungi, bacteria or protozoa which comprises applying to a host subject an antimicrobially effective amount of a compound of the formula

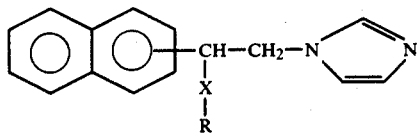

(I)

wherein:
R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl; and X is oxygen or sulfur; or a pharmaceutically acceptable acid addition salt thereof; or a composition containing such compound as an active ingredient.

27. The method of claim 26 wherein the compound of formula (I) is administered topically.

28. A pharmaceutical composition for inhibiting the growth of fungi, bacteria or protozoa which comprises an antimicrobially effective amount of a compound of the formula

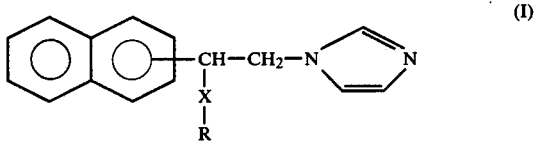

(I)

wherein:
R is alkyl having from 1 to 12 carbon atoms, benzyl, substituted benzyl, phenyl or substituted phenyl, said substituted benzyl and substituted phenyl substituted on the phenyl ring with from one to three substituents independently selected from the group consisting of halo, lower alkyl having from 1 to 4 carbon atoms, and trifluoromethyl;

X is oxygen or sulfur; or a pharmaceutically acceptable acid addition salt thereof; in admixture with a pharmaceutically acceptable, non-toxic carrier.

* * * * *